United States Patent [19]

Nohara et al.

[11] 4,085,116
[45] Apr. 18, 1978

[54] NOVEL CHROMONE DERIVATIVES

[75] Inventors: Akira Nohara, Kyoto; Toshihiro Ishiguro, Osaka; Yasushi Sanno, Ikeda, all of Japan

[73] Assignee: Takeda Chemical Industries, Ltd., Japan

[21] Appl. No.: 669,973

[22] Filed: Mar. 24, 1976

[30] Foreign Application Priority Data

Apr. 11, 1975 United Kingdom ............... 15061/75

[51] Int. Cl.$^2$ .................... A61K 31/41; C07D 257/04
[52] U.S. Cl. .................................. 260/308 D; 424/269
[58] Field of Search .................................... 260/308 D

[56] References Cited

U.S. PATENT DOCUMENTS 3,896,114  7/1975  Nohara ........................... 260/308 D Primary Examiner—Frederick E. Waddell
Attorney, Agent, or Firm—Wenderoth, Lind & Ponack

[57] ABSTRACT

The present invention relates to novel chromone derivatives having effective antiallergic action with low toxicity, which are shown by the following formula (I)

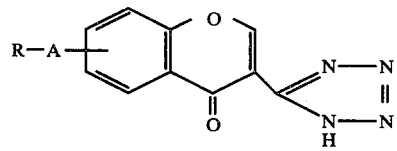

wherein R is hydrogen or lower alkyl and A is (R' is hydrogen or lower alkyl) or

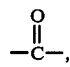

and their physiologically acceptable salts.

5 Claims, No Drawings

NOVEL CHROMONE DERIVATIVES

The present invention relates to novel chromone derivatives which have excellent pharmacological activities. More particularly, the present invention provides novel chromone derivatives of the formula (I)

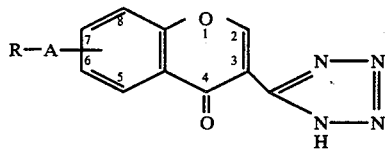

wherein R is hydrogen or lower alkyl and A is

(R' is hydrogen or lower alkyl) or

and their physiologically acceptable salts, which have excellent pharmacological activities such as anti-allergic activity. The present invention also provides industrially feasible methods for the production of these compounds as well as pharmaceutical compositions comprising these compounds.

In the formula (I), the compounds having some of substituents, for example 1-hydroxyethyl, 1-hydroxypropyl, 1-methyl-1-hydroxybutyl, represented by R—A— exist in two isomeric forms, i.e. dextro- and levorotatory isomers. Both the substantially pure dextro-and levorotatory isomers of these compounds, as well as the racemic mixtures are considered to be an integral part of this invention.

The above-mentioned chromone derivatives (I) may be produced by process chosen from the following Processes A to D, depending upon their substituents.

Process A

The compounds of the formula

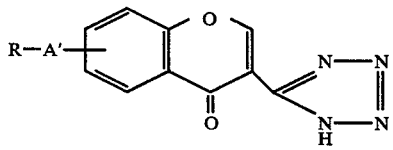

wherein R has the same meaning as defined above and A' is

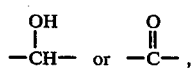

and their salts, may be produced by reacting the compounds of the formula (II)

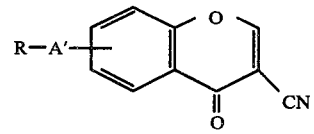

wherein R and A' have the same meaning as defined above, with hydrazoic acid or a salt thereof.

Process B

The compounds of the formula (I-2)

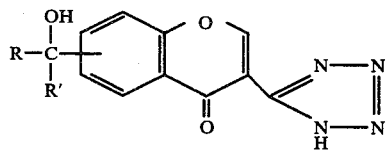

wherein R and R' have the same meaning as defined above and their salts, may be produced by hydrolyzing the compounds of the formula (III)

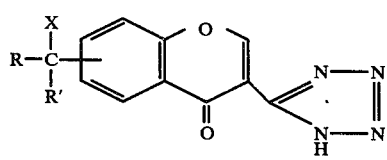

wherein R and R' have the same meaning as defined above and X is a group which can be converted into hydroxyl by hydrolysis.

Process C

The compounds of the formula (I-3)

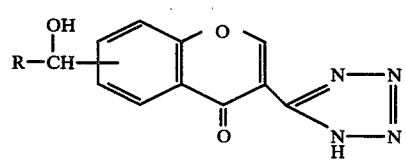

wherein R has the same meaning as defined above and their salts, may be produced by reducing the compounds of the formula (I-4)

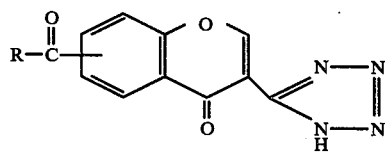

wherein R has the same meaning as defined above.

Process D

The compounds of the above-mentioned formula (I-4) and their salts, may be produced by oxidizing the compounds of the above-mentioned formula (I-3).

The substituents designated in each of the abovementioned formulae may be substituted at an optional position of the 5-, 6-, 7- and 8-positions of the chromone ring. R in each of the formulae is hydrogen or lower alkyl. The lower alkyl for R may be straight or branched, and exemplified by methyl, ethyl, propyl, isopropyl, butyl, iso-butyl, tert.-butyl, pentyl, hexyl and the like. Among them, for practical purposes, lower alkyl having up to 4 carbon atoms are advantageous. Referring to the formulae (I), (I-2) and (III), the lower alkyl represented by the symbol R' is advantageously straight one having up to 3 carbon atoms, i.e. methyl, ethyl or propyl.

The Processes A to D will be explained in detail below:

Process A

This process is carried out by reacting a compound of the formula (II) with hydrazoic acid or a salt thereof.

In this reaction, when there is employed a compound of the formula (II) in which R—A'— stands for carboxaldehyde group (hereinafter referred to as compound (II-1)), if necessary, the carboxaldehyde group may be protected by converting the compound (II-1) into dialkylacetal (e.g. dimethylacetal), diacyl ester (e.g. diacetyl ester), 1,3-dioxolan or the like.

Such protection may be conducted by per se known procedures and, for example, the dimethylacetal is prepared by reacting the compound (II-1) with methyl orthoformate in the presence of hydrogen chloride, the diacetyl ester is prepared by reacting the compound (II-1) with acetic anhydride in the presence of acetic acid and 1,3-dioxolan is prepared by reacting the compound (II-1) with ethyleneglycol in the presence of p-toluenesulfonic acid.

After the desired reaction, such protected carboxaldehyde group can easily be led into unprotected carboxaldehyde group by procedures which are conventional per se, such as hydrolysis with a suitable acid (e.g. hydrochloric acid).

The salt of hydrazoic acid which is employed in this reaction includes, among others, the salts of hydrazoic acid with alkali metals such as lithium azide, sodium azide, potassium azide, etc.; the salts of hydrazoic acid with alkaline earth metals such as magnesium azide, calcium azide, barium azide, strontium azide, etc.; the salts of hydrazoic acid with other metals capable of forming salts with hydrazoic acid such as aluminum azide, tin azide, zinc azide, titanium azide, etc.; and the salts of hydrazoic acid with ammonia or organic amines (e.g. aniline). In addition an alkali metal salt of hydrazoic acid, e.g. sodium azide, is used in combination with, for example, a Lewis acid such as aluminum chloride, stannic chloride, zinc chloride or titanium tetrachloride or with ammonium chloride. It appears that, in such cases, the alkali metal salt of hydrazoic acid is converted to a hydrazoic acid salt of the cation of the adjunct compound, such as aluminum azide, tin azide, zinc azide, titanium azide or ammonium azide, and, then, this hydrazoic acid salt reacts with the starting compound of the formula (II). The amount of hydrazoic acid, a salt thereof or the Lewis acid or equivalent which is used in combination with the salt is generally about 1 to 7 moles per mole of the starting compound (II) for practical purposes.

Generally, the reaction is desirably carried out in an organic solvent. The solvent is exemplified by hydrocarbons such as benzene, toluene, petroleum ether, etc.; ethers such as tetrahydrofuran, dioxane, ethyl ether, ethylene glycol dimethyl ether, etc.; acetonitrile; dimethylformamide; formamide; dimethylsulfoxide; etc. While the reaction conditions including temperature and time factors are largely optional, it is generally convenient to carry out the reaction at room temperature to about 150° C for about 1 hour to about 2 days.

When a salt of hydrazoic acid is used as one of the starting compounds, the reaction yields the object compound of the formula (I-1) in the form of salts corresponding to the hydrazoate used due to the acid function of the tetrazole ring. This salt, however, can be easily converted to the object compound (I-1) possessing a free tetrazole ring by treating it with a suitable acid (e.g. a mineral acid such as hydrochloric acid or sulfuric acid).

Process B

This process is conducted by hydrolyzing the compound of the formula (III). In the formula (III) X stands for a group which can be converted into hydroxyl by hydrolysis. Representatives of such groups are halogen atoms and acyloxy groups. As the halogen atoms there may be mentioned chlorine, bromine, iodine and fluorine. The acyloxy group may be preferably a lower alkylcarbonyloxy group whose alkyl moiety has 1 to 3 carbon atoms (e.g. acetoxy, propionyloxy and butyryloxy), or an arylcarbonyloxy group (e.g. benzoyloxy).

The hydrolysis of this process is generally performed by allowing an aqueous solution of a base or an acid to react upon the compoumd (III). The base which is employed in this reaction, among others, includes metal hydroxides such as potassium hydroxide, sodium hydroxide, barium hydroxide, lithium hydroxide, calcium hydroxide, etc. and inorganic or organic ammonium hydroxides such as ammonium hydroxide, tetramethylammonium hydroxide, etc. As the acid there may be advantageously employed inorganic acids such as hydrochloric acid, sulfuric acid, hydrobromic acid, etc.; and organic acids such as acetic acid. These bases or acids are employed in an amount from about 2 to about 20 moles of the starting compound (III) for practical purposes. While the reaction conditions including temperature and time factor are largely optional, it is generally convenient to carry out the reaction at room temperature to about 100° C for about 1 hour to about 1 day.

When a hydroxide is used as the reagent, the reaction yields the object compound of the formula (I-2) in the form of salts corresponding to the hydroxide used due to the acid function of the tetrazole ring. This salt, however, can be easily converted to the object compound (I-2) possessing a free tetrazole ring by treating it with a suitable acid (e.g. a mineral acid such as hydrochloric acid or sulfuric acid).

Process C

This process consists in reducing the compound of the formula (I-4) belonging to the object compound (I) to obtain the compound of the formula (I-3) which also falls within the formula (I). The reduction reaction in this process is carried out generally in the presence of water or an organic solvent (such as, methanol, ethanol, ethyl ether, dioxane, benzene, etc.). As for the specific reduction procedures, mention may be made, for example, for catalytic reduction with a catalyst such as platinum, palladium or the like, reduction with a metal hydride such as lithium aluminum hydride, lithium borohydride, lithium cyanoborohydride, sodium borohydride, sodium cyanoborohydride or the like, Meerwein-Poundorf-Verley reduction involving the employment of aluminum isopropoxide or the like, reduction by means of sodium metal, magnesium metal or the like and an alcohol, reduction with zinc dust and a base, reduction by means of a metal, e.g. iron, zinc or the like, in combination with an acid, e.g. hydrochloric acid, acetic acid or the like, electrolytic reduction, reduction with the aid of a reductase enzyme, etc. Aside from the aforementioned procedures, any other means capable of reducing a carbonyl group to an alcoholic hydroxyl may likewise be employed. While the operable reaction temperature varies with different reduction procedures selected, ordinarily it is preferably within the range of about -20° to about 100° C. The present reaction can be successfully conducted at atmospheric pressure but, if necessary, it may be carried out at an elevated or reduced pressure. The solvents mentioned hereinbefore may be used alone or in combination, and any other solvent may also be employed insofar as it does not interfere with the contemplated reaction.

Process D

In this process there may be employed any oxidation means capable of oxidizing the alcoholic hydroxyl of the compound (I-3) to a carbonyl group. Generally, the oxidation reaction is conducted by allowing an oxidizing agent to react upon the compound (I-3) in an acidic condition. As the oxidizing agent there may be mentioned, for example, chromium trioxide, potassium dichromate, potassium permanganate, manganese dioxide, etc. This oxidation reaction is generally conducted in the presence of an organic solvent. As the organic solvent there may be conveniently employed, for example, ketones (e.g. acetone, methyl ethyl ketone, etc.), dimethylformamide, formamide, etc., and any other organic solvent may also be employed insofar as it does not interfere with the contemplated oxidation reaction. While the reaction conditions including temperature and time factor are largely optional, it is generally advantageous to conduct the reaction at about 0° C to about 100° C, especially in the neighbourhood of room temperature, for about 5 minutes to about 2 days. As the acid which is employed to attain the acidic conditions, there may be practically employed mineral acids such as sulfuric acid, hydrochloric acid, etc.

By any of the above-mentioned Processes A to D, the object compound (I) is produced which can be easily recovered by a per se conventional means such as extraction, chromatography, recrystallization, etc. The object compound (I) can be recovered either in the free state or in a form of salts. For example, the object compound (I) may be converted to an organic amine salt, alkali metal salt or ammonium salt by reacting the compound (I) with an organic amine, e.g. monoethanolamine, diethanolamine, dl-methylephedrine, 1-(3,5-dihydroxyphenyl)-L-isopropylaminoethanol, isoproterenol, dextromethorphan, Hetrazan (diethylcarbamazine), diethylamine, or triethylamine, pyrrolidine, piperidine; an alkali metal hydroxide, e.g. sodium hydroxide or potassium hydroxide; or ammonia as the case may be in a per se conventional manner, e.g. by admixing and heating the reactants together in the presence of an appropriate solvent.

The compounds of the formula (I) and their physiologically acceptable salts which can be produced by the foregoing procedure have strong antiallergic properties with low toxicity and are of use as drugs for the prevention and treatment of allergic diseases such as allergic asthma, allergic dermatitis and hay fever. Further, since the alkali metal salts and organic amine salts are highly soluble in water and the solutions so formed are stable, they lend themselves well to manufacturing such pharmaceutical preparations as injections and solutions.

When a compound of the formula (I) or a salt thereof is uses as, for example, a drug for the prevention and treatment of the above-mentioned allergic diseases, it can be administered orally as tablets, capsules, powders or solutions or in such optional dosage forms as injections, aerosol inhalants or ointments, usually at a daily human adult dosage of about 1 to 500 milligrams.

Compounds of the formula (III) which are used as one of the starting compounds in the present invention can be produced by, for example, the following procedures:

a. The compound of the formula (III) wherein X is, e.g. bromine, is produced by reacting the compound of the formula

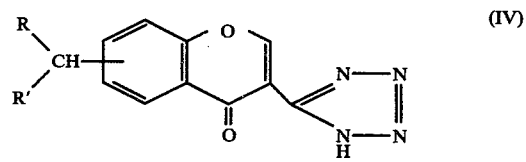

[wherein R and R' have the same meaning as defined above] which is a per se known compound (Japanese Patent Application No. 37235/1972 laid open to public inspection on Dec. 25, 1973 under Patent Application Laid Open No. 103578/1973) with N-bromosuccinimide (hereinafter briefly referred to as NBS). The amount of NBS which is used in this reaction is generally about 1 to 2 moles per mole of the compound (IV). The reaction is desirably conducted in an organic solvent such as chloroform, tetrachloromethane, dichloromethane, tetrachloroethane. While the reaction conditions are largely optional, it is generally advantageous to carry out the reaction at a temperature near the boiling point of the solvent employed under irradiation of infrared ray for about 5 minutes to about 24 hours. The thus-produced compound of the formula (III) wherein X is bromine may be conveniently subjected, without being isolated but in a form of the reaction mixture, to the hydrolysis reaction of Process B.

b. The compound of the formula (III) wherein X is, e.g. acetoxy, is produced by the following procedure.

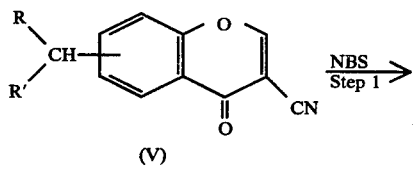

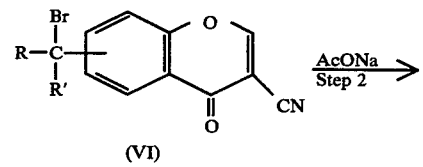

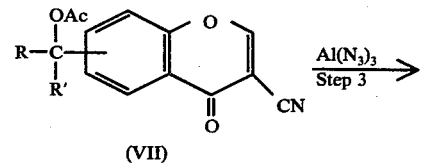

-continued

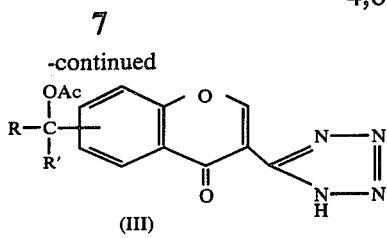

[wherein Ac means acetyl, and R and R' have the same meaning as defined above].

More particularly, the compound of the formula (V) which is a per se known compound (the above-mentioned Japanese Patent Application Laid Open No. 103578/1973) is reacted with NBS under irradiation of infrared ray [Step 1], the resulting compound (VI) is reacted with sodium acetate to obtain the compound (VII) [Step 2], which is then reacted with hydrazoic acid or a salt thereof in the manner mentioned in connection with Process A to obtain the compound of the formula (III) wherein X is acetoxy [Step 3]. The compound of the formula (III) wherein X is acetoxy may be produced also by reacting the compound of the formula (III) wherein X is bromine with sodium acetate.

The compounds of the formula (III) are also novel compounds. They have excellent anti-allergic activity and are of use as drugs for the prevention and treatment of allergic diseases such as allergic asthma, allergic dermatitis and hay fever similarly to the compounds of the formula (I).

The compounds of the formula (II) may be produced by, for example, the following procedure:

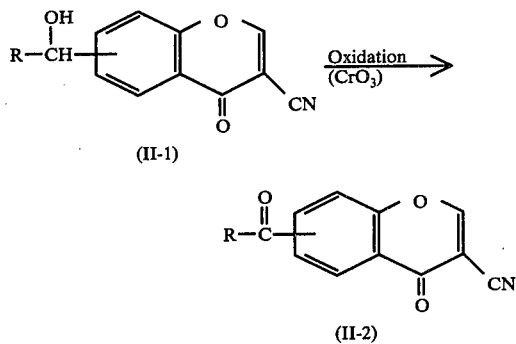

[wherein R has the same meaning as defined above].

The following Examples as well as Reference Examples are merely for illustrative purposes and not to be construed as the limitation of the present invention.

In the following Reference Examples and Examples the terms "part(s)" means "weight part(s)" unless otherwise specified, and the relationship between "part(s)" and "part(s) by volume" corresponds to that between gram(s) and milliliter(s).

REFERENCE EXAMPLE 1 a. A mixture of 9.95 parts of 6-ethyl-4-oxo-4H-1-benzopyran-3-carbonitrile 8.90 parts of NBS and 300 parts by volume of tetrachloromethane is refluxed under stirring and irradiation of infrared ray (100 volt, 375 WR) for 2 hours. The tetrachloromethane is distilled off and the solid residue is well shaken with 500 parts by volume of ethyl acetate and 100 parts by volume of water. The ethyl acetate layer is collected and shaken with 100 parts by volume of water. In this manner, the ethyl acetate layer is repeatedly washed with water until the solid residue disappears. The ethyl acetate layer is dried on $Na_2SO_4$, concentrated and cooled. The procedure yields 12.11 parts of 6-(1-bromoethyl)-4-oxo-4H-1-benzopyran-3-carbonitrile as colorless crystals. Melting point: 162-164° C Elemental analysis for $C_{12}H_8BrNO_2$ Calculated: C, 51.82; H, 2.90; N, 5.04 Found: C, 51.89; H, 2.81; N, 5.14 b. A mixture of 5.56 parts of 6-(1-bromoethyl)-4-oxo-4H-1-benzopyran-3-carbonitrile, 1.640 parts of anhydrous sodium acetate and 8 parts by volume of dimethylformamide is heated at 70° C under stirring for 50 minutes. After cooling, the reaction mixture is poured into 100 parts by volume of water to give precipitates, which are collected and recrystallized from ethanol and subsequently ethyl acetate. The procedure yields 2.90 parts of 6-(1-acetoxy-ethyl)-4-oxo-4H-1-benzopyran-3-carbonitrile. Melting point: 148°-149° C Elemental analysis for $C_{14}H_{11}NO_4$ Calculated: C, 65.36; H, 4.31; N, 5.45 Found: C, 65.15; H, 4.34; N, 5.30 c. To a mixture of 45 parts by volume of tetrahydrofuran and 4.005 parts of anyhydrous aluminum chloride there are added 3.86 parts of 6-(1-acetoxyethyl)-4-oxo-4H-1-benzopyran-3-carbonitrile and 2.925 parts of sodium azide, and the resulting mixture is refluxed under stirring for 1.5 hours. After cooling, the solvent is distilled off. To the solid residue are added 2.1 parts of sodium nitrite and ice-water, and the mixture is well shaken. The insoluble material is recovered by filtration and recrystallized from ethyl acetate. The procedure yields 1.88 parts of 6-(1-acetoxyethyl)-3-(1H-tetrazol-5-yl)-chromone as colorless crystals. Melting point: 231°-232° C Elemental analysis for $C_{14}H_{12}N_4O_4$ Calculated: C, 56.00; H, 4.03; N, 18.66 Found: C, 55.88; H, 3.91; N, 18.50

REFERENCE EXAMPLE 2 a. A mixture of 1.43 parts of 6-(1-acetoxyethyl)-4-oxo-4H-1-benzopyran-3-carbonitrile and 25 parts by volume of 1N-sodium hydroxide is stirred at room temperature for 80 minutes. After being acidified with 1N-hydrochloric acid, the reaction mixture is extracted with ethyl acetate. The ethyl acetate layer is washed with water and dried on $Na_2SO_4$. The ethyl acetate is distilled off and the resulting residue is recrystallized from ethyl acetate. The procedure yields 0.790 part of 6-(1-hydroxyethyl)-4-oxo-4H-1-benzopyran-3-carbonitrile as colorless crystals. Melting point: 147°-148° C Elemental analysis for $C_{12}H_9NO_3$ Calculated: C, 66.97; H, 4.22; N, 6.51 Found: C, 66.91; H, 4.06; N, 6.28 b. To a solution of 0.645 part of 6-(1-hydroxyethyl)-4-oxo-4H-1-benzopyran-3-carbonitrile in 20 parts by volume of acetone under stirring at room temperature is added dropwise over a period of 1 hour 1.0 part by volume of a solution which is prepared from chromium trioxide, 97% sulfuric acid and water in a ratio of 6.0 parts: 3.6 parts by volume: 18 parts by volume. The dark-green resins precipitated in the flask bottom is separated from the reaction mixture by decantation, and the solution is concentrated at room temperature to a one-third volume and then admixed with water to give precipitates. The precipitates collected by filtration is washed with water and recrystallized from ethyl acetate. The procedure yields 0.440 part of 6-acetyl-4-oxo-4H-1-benzopyran-3-carbonitrile as colorless crystals. Melting point: 170°–172° C Elemental analysis for $C_{12}H_7NO_3$ Calculated: C, 67.60; H, 3.31; N, 6.57 Found: C, 67.71; H, 3.33; N, 6.41

REFERENCE EXAMPLE 3

To a solution of 9.25 parts of 6-methyl-4-oxo-4H-1-benzopyran-3-carbonitrile in a mixture of 100 parts by volume of acetic acid, 100 parts by volume of acetic anhydride and 10 parts by volume of 97% sulfuric acid kept at 5°–10° C, there was added 15.5 parts of chromium trioxide over a period of 4 hours under stirring. The reaction mixture was poured into 1500 parts by volume of ice-water to give precipitates, which were collected by filtration, washed with water and recrystallized from ethanol. The procedure yielded 8.19 parts of 6-diacetoxymethyl-4-oxo-4H-1-benzopyran-3-carbonitrile as colorless needles. Melting point: 185°–186° C Elemental analysis for $C_{15}H_{11}NO_6$ Calculated: C, 59,80; H, 3.68; N, 4.65 Found: C, 60.01; H, 3.93; N, 4.52

Infrared absorption spectrum $\nu_{max}^{KBr}$ cm$^{-1}$ : 2245(CN), 1765 (OAc), 1665 (CO)

Nuclear magnetic resonance spectrum (DMSO-d$_6$) δ : 9.19(1H,s), 8.15(1H,m), 8.02(1H,dd), 7.78(1H,d, J=9Hz), 7.65(1H,s), 2.14(6H,s)

EXAMPLE 1

A mixture of 12.10 parts of 6-ethyl-3-(1H-tetrazol-5-yl)chromone, 13.4 parts of NBS and 500 parts by volume of chloroform is refluxed under stirring and irradiation of infrared ray (100 volt, 375 WR) for 15 minutes. After cooling, the insoluble material is collected by filtration and washed with a small amount of chloroform. The resulting solid is confirmed to contain 6-(1-bromoethyl)-3-(1H-tetrazol-5-yl)chromone in that it has a proton of methyl (d,J=7Hz) at δ 2.06 and a proton of methine (q,J=7Hz) at δ 5.67 in its nuclear magnetic resonance spectrum (DMSO-d$_6$).

The solid is suspended in 1000 parts by volume of 1N-sodium hydroxide and stirred at room temperature for 165 minutes. The resulting pale-yellow solution is adjusted to pH 5.0 with concentrated hydrochloric acid and shaken with chloroform to remove the remaining starting materials. The resulting aqueous layer is treated with activated carbon and adjusted to pH 1.0 with 1N-hydrochloric acid to give precipitates. The precipitates are recovered by filtration, recrystallized from ethanol and washed with water. The procedure yields 6.89 parts of 6-(1-hydroxyethyl)-3-(1H-tetrazol-5-yl)chromone as colorless crystals. Melting point: 234°–236° C(decomposition with foaming)

Elemental analysis for $C_{12}H_{10}N_4O_3$
Calculated: C, 55.81; H, 3.90; N, 21.70
Found: C, 55.71; H, 3.69; N, 21.82

Nuclear magnetic resonance spectrum (DMSO-a$_6$) δ: 9.21(1H,s), 8.17(1H,d,J=2Hz), 7.54–8.30(3H,m), 4.92 (1H,q,J=7Hz), 1.43(3H,d,J=7Hz)

By procedures similar to the procedure described above, the following compounds are produced.

| Starting compound | Product | Melting point (° C) |
|---|---|---|
| 6-propyl-3-(1H-tetrazol-5-yl)-chromone | 6-(1-hydroxypropyl)-3-(1H-tetrazol-5-yl)-chromone | 214–215 |
| 6-butyl-3-(1H-tetrazol-5-yl)-chromone | 6-(1-hydroxybutyl)-3-(1H-tetrazol-5-yl)-chromone | 216–218 (decomp. with foaming) |
| 6-isopropyl-3-(1H-tetrazol-5-yl)chromone | 6-(1-methyl-1-hydroxyethyl)-3-1H-tetrazol-5-yl)chromone | 245–246 (decomp. with foaming) |

EXAMPLE 2

A mixture of 0.258 part of 6-(1-hydroxyethyl)-3-(1H-tetrazol-5-yl)chromone, 0.14 part by volume of diethanolamine and 5 parts by volume of ethanol is heated to give a solution. To the solution is added diethyl ether in an amount sufficient to form precipitates. The mixture is kept standing in a refrigerator and the resulting crystals are recovered by filtration and recrystallized from a mixture of ethanol and diethyl ether. The procedure yields 0.280 part of diethanolamine salt of 6-(1-hydroxyethyl)-3-(1H-tetrazol-5-yl)chromone as colorless crystals. Melting point: 139°–141° C Elemental analysis for $C_{16}H_{21}N_5O_5$ Calculated: C, 52.88; H, 5.83; N, 19.28 Found: C, 52.81; H, 5.85; N, 19.22

By a procedure similar to the procedure described above pyrrolidine salt of 6-(1-hydroxyethyl)-3-(1H-tetrazol-5-yl)chromone is obtained as colorless crystals melting at 162°–168° C(decomposition with foaming).

EXAMPLE 3

A solution of 0.300 part of 6-(1-acetoxyethyl)-3-(1H-tetrazol-5-yl)chromone in 4 parts by volume of 1N-NaOH is stirred at room temperature for 1 hour and then acidified with 1N-hydrochloric acid. The resulting precipitates are recovered by filtration and recrystallized from ethanol to obtain 0.100 of 6-(1-hydroxyethyl)-3-(1H-tetrazol-5-yl)chromone as colorless crystals melting at 234°–236° C (decomposition with foaming).

EXAMPLE 4

To a solution of 2.58 parts of 6-(1-hydroxyethyl)-3-(1H-tetrazol-5-yl)chromone in 700 parts by volume of acetone kept at 9°–15° C there is added dropwise over a period of 30 minutes 4.5 parts by volume of a solution which is prepared from chromium trioxide, 97% sulfuric acid and water in a ratio of 6.0 parts: 3.6 parts by volume: 18 parts by volume. The reaction mixture is concentrated at a temperature lower than 30° C to a one-tenth volume and then admixed with 700 parts by volume of water to give precipitates. The precipitates are recovered by filtration and recrystallized from dimethylformamide. The procedure yields 1.70 parts of 6-acetyl-3-(1H-tetrazol-5-yl)chromone as colorless crystals.

Elemental analysis for $C_{12}H_8N_4O_3$ Calculated: C, 56.25; H, 3.15; N, 21.87 Found: C, 55.95; H, 3.30; N, 21.98 Infrared absorption spectrum $\nu_{max}^{KBr}$ cm$^{-1}$: 1685, 1635

Nuclear magnetic resonance spectrum (DMSO-d$_6$) δ: 9.28(1H,s,H$_2$), 8.68(1H,d,J=2Hz,H$_5$), 8.38(1H,dd,J=2 and 8Hz,H$_7$), 7.87(1H,d,J=8Hz,H$_8$), 2.68(3H,s,Ac). Mass spectrum m/e: 256(M$^+$), 200, 185(base peak), 157,129

By a procedure similar to that described in Example 2, pyrrolidine salt of 6-acetyl-3-(1H-tetrazol-5-yl)-chromone is obtained.

Elemental analysis for $C_{16}H_{17}N_5O_3$ Calculated: C, 58.70; H, 5.23; N, 21.40 Found: C, 58.69; H, 4.96; N, 21.25

Nuclear magnetic resonance spectrum (DMSO-$d_6$+$D_2O$) δ: 8.78(1H,s), 8.63(1H,d,J=2Hz), 8.23(1H,dd,J=2 and 9 Hz), 7.76(1H,d,J=9Hz), 3.25(4H,t,J=7Hz), 2.65 (3H,s), 1.92(4H,m)

EXAMPLE 5

To 40 parts by volume of tetrahydrofuran are added under cooling 4.0 parts of anhydrous aluminum chloride, 3.20 parts of 6-acetyl-4-oxo-4H-1-benzopyran-3-carbonitrile and 2.93 parts of sodium azide in the order mentioned and, under stirring, the mixture is refluxed for 30 minutes. After cooled, the reaction mixture is concentrated to dryness. To the residue are added 100 parts by volume of 1N-hydrochloric acid and 3.10 parts of sodium nitrite, and the insoluble material is recovered by filtration and recrystallized four times from dimethylformamide to obtain 0.380 part of 6-acetyl-3-(1H-tetrazol-5-yl)-chromone as colorless crystals.

By a procedure similar to the procedure described above 6-(1-hydroxyethyl)-3-(1H-tetrazol-5-yl)chromone is obtained from 6-(1-hydroxyethyl)-4-oxo-4H-1-benzopyran-3-carbonitrile.

EXAMPLE 6

To a suspension of 0.128 part of 6-acetyl-3-(1H-tetrazol-5-yl)chromone in 5 parts by volume of methanol is added under stirring 0.020 part of sodium borohydride. The resulting mixture is stirred at room temperature for 2 minutes and then refluxed for 2 minutes. The solvent is distilled off and to the residue is added 10 parts by volume of 1N-hydrochloric acid. The resulting precipitates are recovered by filtration and recrystallized twice from ethanol to obtain 0.013 part of 6-(1-hydroxyethyl)-3-(1H-tetrazol-5-yl)chromone as colorless crystals melting at 234°-236° C(decomposition with foaming).

EXAMPLE 7

To 3 parts by volume of tetrahydrofuran was added under cooling 0.267 part of pulverized anhydrous aluminum chloride, 0.301 part of 6-diacetoxymethyl-4-oxo-4H-1-benzopyran-3-carbonitrile and 0.195 part of sodium azide in the order mentioned and the resulting mixture was refluxed under stirring for 1.5 hours. After cooling, to the mixture there were further added 0.133 part of anhydrous aluminum chloride and 0.098 part of sodium azide and, under stirring, the resulting mixture was again refluxed for 1 hour.

Then, the solvent was distilled off. To the residue was added 20 parts by volume of 1N-hydrochloric acid, and the insoluble material was recovered by filtration and was suspended in a mixture-solution of 5 parts by volume of acetic acid and 5 parts by volume of 1N-hydrochloric acid and, under stirring, refluxed for 15 minutes. After cooling, the insoluble material was collected by filtration, washed with water and then ethyl acetate and recrystallized from dimethylformamide-water to obtain 0.140 part of 3-(1H-tetrazol-5-yl) chromone-6-carboxaldehyde as pale yellow plates. Melting point: 283°-286° C(decomposition)

Elemental analysis for $C_{11}H_6N_4O_3$ Calculated: C, 54.55; H, 2.50; N, 23.14 Found: C, 54.28; H, 2.54; N, 23.34

Infrared absorption spectrum $\nu_{max}^{KBr}$ cm$^{-1}$: 3260(NH), 1700(CO), 1650(CO)

Nuclear magnetic resonance spectrum (CF$_3$COOD) δ: 9.78(1H,s), 9.12(1H,s), 8.67(1H,d,J=1.5Hz), 8.02 (1H,dd), 7.59(1H,d,J=9Hz)

EXAMPLE 8

A suspension of 0.242 part of 3-(1H-tetrazol-5-yl)chromone-6-carboxaldehyde in 5 parts by volume of methanol was heated to dissolve the starting compound as much as possible. To the solution under stirring was added little by little 0.038 part of sodium borohydride under warming to obtain a nearly homogeneous solution. The resulting solution was again heated to dissolve completely, and then to the resulting solution was further added little by little 0.019 part of sodium horohydride under warming. The solvent was distilled off, and to the residue was added 20 parts by volume of 1N-hydrochloric acid. The resulting pale yellow precipitates were recovered by filtration and recrystallized from ethanol to obtain 0.090 part of 6-hydroxymethyl-3-(1H-tetrazol-5-yl)chromone as pale yellow crystals. Melting point: 264°-266° C(decomposition)

Elemental analysis for $C_{11}H_8N_4O_3$ Calculated: C, 54.10; H, 3.30; N,22.94 Found: C, 54.10; H, 3.29; N,22.99

Infrared absorption spectrum $\nu_{max}^{KBr}$ cm$^{-1}$: 3325, 1660(CO)

Nuclear magnetic resonance spectrum (DMSO-$d_6$)δ: 9.22(1H,s), 8.13(1H), 7.55-7.95(2H,m), 4.65(2H,s)

EXAMPLE 9

Some examples of pratical recipes in which the compounds of this invention are utilized as remedies for an allergic disease are as follows.

A. (Tablet)

| | |
|---|---|
| (1) 6-(1-hydroxyethyl)-3-(1H-tetrazol-5-yl)chromone | 20 mg. |
| (2) lactose | 35 mg. |
| (3) corn starch | 150 mg. |
| (4) microcrystalline cellulose | 30 mg. |
| (5) magnesium stearate | 5 mg. |
| | 240 mg. per tablet |

(1), (2), (3), ⅔ quantity of (4) and half quantity of (5) are throughly mixed, and then the mixture is granulated. Remaining ⅓ quantity of (4) and half of (5) are added to the granules and compressed into tablets. Thus prepared tablets can further be coated with a suitable coating agent, e.g. sugar.

B. (Capsule)

| | |
|---|---|
| (1) 6-acetyl-3-(1H-tetrazol-5-yl)chromone | 20 mg. |
| (2) lactose | 102 mg. |
| (3) microcrystalline cellulose | 70 mg. |
| (4) magnesium stearate | 8 mg. |
| | 200 mg. per capsule |

(1), (2), (3) and half quantity of (4) are throughly mixed, and then the mixture is granulated. Remaining half of (4) is added to the granules and the whole is filled into a gelatin capsule.

| C. (Injection) | |
|---|---|
| (1) Sodium salt of 6-hydroxymethyl-3-(1H-tetrazol-5-yl)chromone | 10 mg. |
| (2) inositol | 100 mg. |
| (3) benzyl alcohol | 20 mg. |

All ingredients are dissolved in water to make 2.0 ml of the solution (pH 7.5) serving as injection.

What we claim is:

1. The compound 6-(1-hydroxyethyl)-3-(1H-tetrazol-5-yl)-chromone.
2. The diethanolamine salt of 6-(1-hydroxyethyl)-3-(1H-tetrazol-5-yl)chromone.
3. The pyrrolidine salt of 6-(1-hydroxyethyl)-3-(1H-tetrazol-5-yl)chromone.
4. The compound 6-acetyl-3-(1H-tetrazol-5-yl)chromone.
5. The pyrrolidine salt of 6-acetyl-3-(1H-tetrazol-5-yl)chromone.

* * * * *